United States Patent [19]

Norton et al.

[11] Patent Number: 5,506,228
[45] Date of Patent: Apr. 9, 1996

[54] 2,6-DIARYL PYRIDAZINONES WITH IMMUNOSUPPRESSANT ACTIVITY

[75] Inventors: Richard Norton, Somerset, N.J.; Mohammed K. A. Ibraham, Imbaba-Giza, Egypt

[73] Assignee: Merck & Co., Inc., Rahway, N.J.

[21] Appl. No.: 392,580

[22] Filed: Feb. 23, 1995

[51] Int. Cl.$^6$ ............................................. A61K 31/50
[52] U.S. Cl. ............................................. 514/247; 544/240
[58] Field of Search ............................ 514/247; 544/240; 504/238

[56] References Cited

U.S. PATENT DOCUMENTS

| | | | |
|---|---|---|---|
| 4,545,810 | 10/1985 | Pyne et al. | 544/240 |
| 5,059,599 | 1/1991 | Mouzin et al. | 544/239 |

FOREIGN PATENT DOCUMENTS

| | | | |
|---|---|---|---|
| 556647 | 8/1993 | European Pat. Off. | 544/240 |

*Primary Examiner*—Donald G. Daus
*Attorney, Agent, or Firm*—Francis P. Bigley; Mark R. Daniel

[57] ABSTRACT

A class of 2,6-diarylpyridazinones of general structural formula I have been identified that exhibit exhibit immunosuppressant activity with human T-lymphocytes, and are useful as an immunosuppressants.

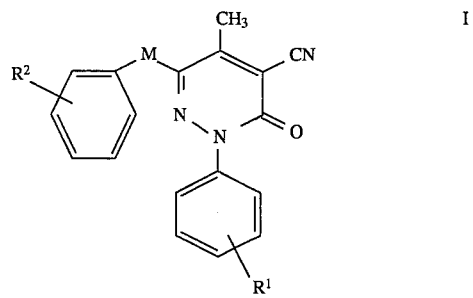

or a pharmaceutically acceptable salt, hydrate or crystal form thereof, wherein:

when M is S, $R^1$ and $R^2$ are selected from the following combinations:
when $R^2$ is 4-chloro, then $R^1$ is 4-OCH$_{3,2}$-CH$_3$, 4-Cl, 4-CH3,
3-Cl, 3-CH3, 2-Cl, 4-H, 4-Br, 3-NO$_2$; and
when $R^2$ is H, then $R^1$ is 4-OCH$_3$, and
when M is —SO$_2$—, then $R^2$ is H and $R^1$ is 4-OCH$_3$.

As an immunosuppressant, these compounds are useful in the treatment of autoimmune diseases, the prevention of rejection of foreign organ transplants and/or related afflictions, diseases and illnesses.

7 Claims, No Drawings

2,6-DIARYL PYRIDAZINONES WITH IMMUNOSUPPRESSANT ACTIVITY

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause undesirable side effects including nephrotoxicity, neurotoxicity, and gastrointestinal discomfort.

SUMMARY OF THE INVENTION

A class of 2,6-diarylpyridazinones of general structural formula are disclosed which exhibit immunosuppressant activity with human T-lymphocytes, and are useful as an immunosuppressants.

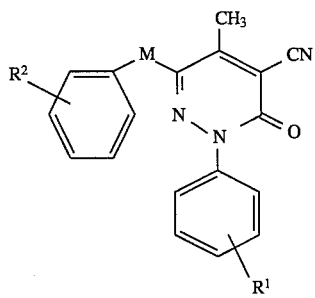

or a pharmaceutically acceptable salt, hydrate or crystal form thereof, wherein:

when M is S, $R^1$ and $R^2$ are selected from the following combinations:
When $R^2$ is 4-chloro, then $R^1$ is 4-OCH$_3$, 2-CH$_3$, 4-Cl, 4-CH3,
3-Cl, 3-CH3, 2-Cl, 4-H, 4-Br, 3-NO$_2$; and
when $R^2$ is H, then $R^1$ is 4-OCH$_3$, and when
M is —SO$_2$—, then $R^2$ is H and $R^1$ is 4-OCH$_3$.

As an immunosuppressant, these compounds are useful in the treatment of autoimmune diseases, the prevention of rejection of foreign organ transplants and/or related afflictions, diseases and illnesses.

DETAILED DESCRIPTION OF THE INVENTION

A class of 2,6-diarylpyridazinones of general structural formula I are disclosed which exhibit immunosuppressant activity with human T-lymphocytes, and are useful as an immunosuppressants.

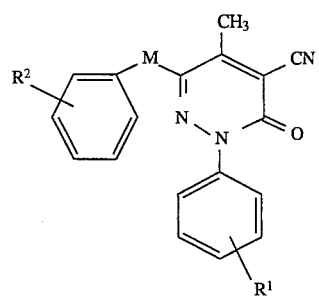

or a pharmaceutically acceptable salt, hydrate or crystal form thereof, wherein:

when M is S, $R^1$ and $R^2$ are selected from the following combinations:
When $R^2$ is 4-chloro, then $R^1$ is 4-OCH$_3$, 2-CH$_3$, 4-Cl, 4-CH3,
3-Cl, 3-CH3, 2-Cl, 4-H, 4-Br, 3-NO$_2$; and
when $R^2$ is H, then $R^1$ is 4-OCH$_3$, and
when M is —SO$_2$—, then $R^2$ is H and $R^1$ is 4-OCH$_3$.

As an immunosuppressant, these compounds are useful in the treatment of autoimmune diseases, the prevention of rejection of foreign organ transplants and/or related afflictions, diseases and illnesses.

The compounds of the present invention may have asymmetric centers and this invention includes all of the optical iomers and mixtures thereof.

In addition compounds with carbon-carbon double bonds may occur in Z- and E- forms with all isomeric forms of the compounds being included in the present invention.

When any variable (e.g., alkyl, aryl, $R^3$, $R^4$, $R^5$, $R^6$, $R^7$, $R^8$, $R^9$, X, Y, Z, X', Y', Z', M, p etc.) occurs more than one time in any variable or in Formula I, its definition on each ocurrence is independent of its definition at every other occurrence.

When a number is used before a substitutent group, it defines the position of that group on the associated phenyl ring. Therefore, when $R^1$ is said to be "4-OCH$_3$", this expression is taken to mean that a methoxy group is located in the para position of the benzene ting to which it is attached.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched- configuration and at least one unsamration, which may occur at any point along the chain, such as ethenyl, propenyl, butenyl, pentenyl, dimethylpentyl, and the like, and includes E and Z forms, where applicable. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tanrote, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

The aryl group may include phenyl or naphthyl which are optionally substituted.

In the instant combination, preferred compounds of formula I are the compounds identified as follows:

| $R^1$ | $R^2$ |
|---|---|
| when M is S, | |
| 4-$OCH_3$ | 4-chloro |
| 2-$CH_3$ | 4-chloro |
| 4-Cl | 4-chloro |
| 4-CH3 | 4-chloro |
| 3-Cl | 4-chloro |
| 3-CH3 | 4-chloro |
| 2-Cl | 4-chloro |
| 4-H | 4-chloro |
| 4-Br | 4-chloro |
| 3-$NO_2$ | 4-chloro; and |
| 4-$OCH_3$ | H, and |
| when M is $-SO_2-$, | H. |
| 4-$OCH_3$ | |

Compounds of this invention can be synthesized using the reaction schemes displayed below:

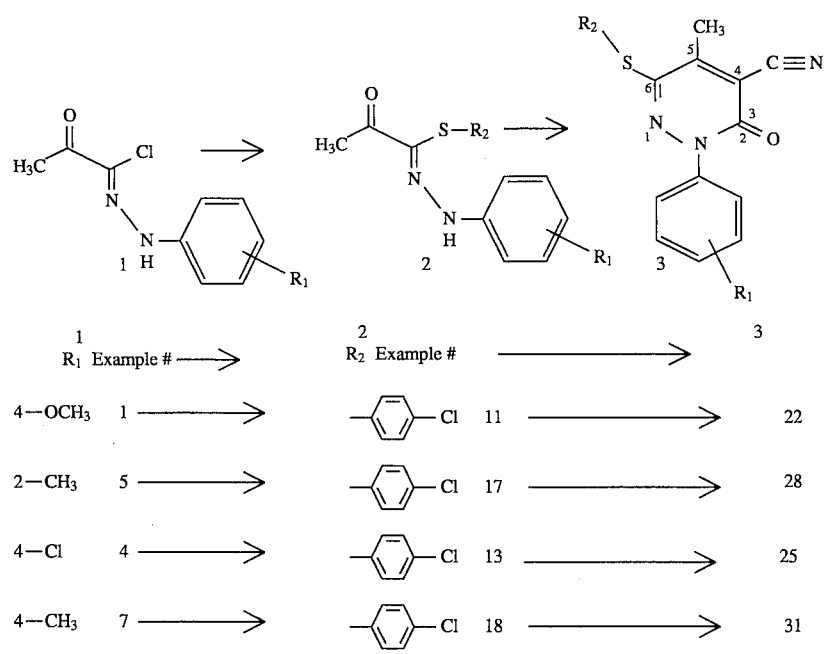

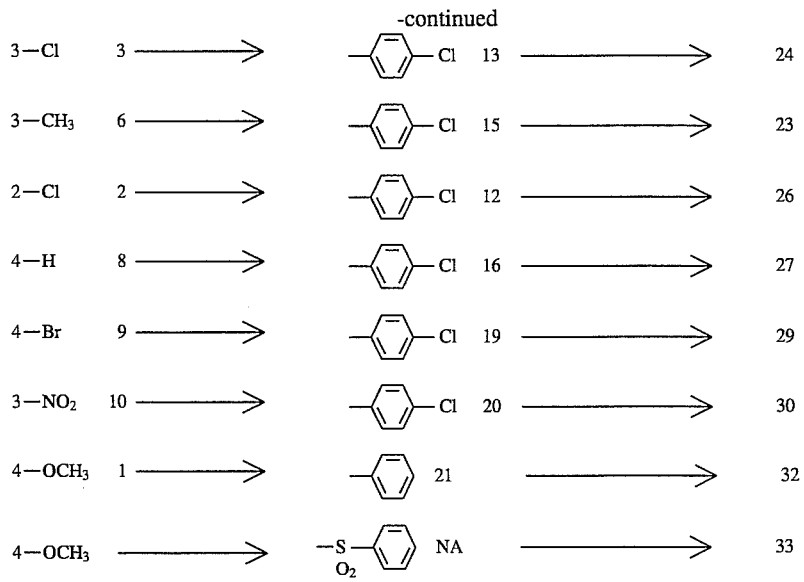

Reaction Scheme A

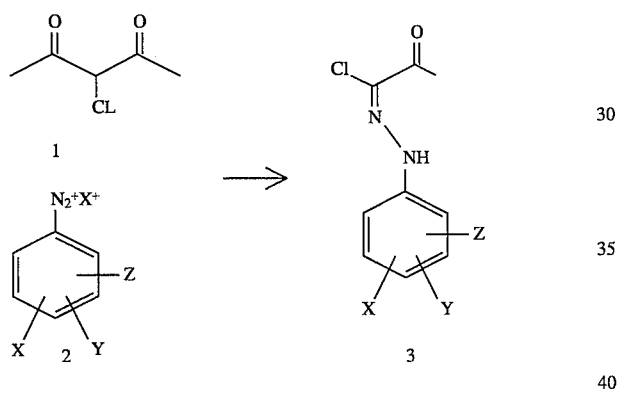

Reaction of commercially available 3-chloropentane-2,4-dione 1 with aryldiazonium salts 2 in the presence of a base such as aqueous sodium acetate gives chloroacetylhydrozone derivatives 3 with loss of acetic acid via an $S_E1$ type mechanism [Org. Reactions 10, 1–142 (1959); J. Am. Chem. Soc., 84, 143–178 (1979)]. The diazonium salts can be conveniently prepared by reacting arylamines with sodium nitrite in acid such as hydrochloric acid or directly with nitrosyl chloride [J. Org. Chem., 26, 5149, 2053 (1961); Org. Syn., 43, 12 (1963)]

Reaction Scheme B

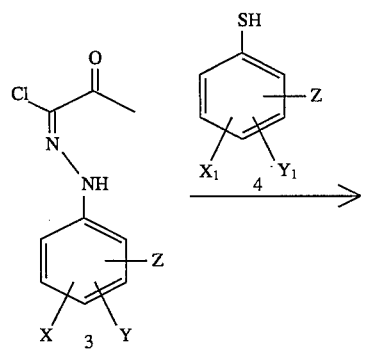

-continued
Reaction Scheme B

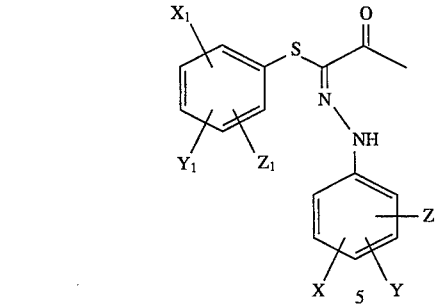

Reaction of chloroacetylhydrazone 3 with arylmercaptan 4 in the presence of a base such as triethylamine in a solvent such as DMF gives thioether 5. Alternatively, the sodium salt of the mercaptan can be prepared and added to 3 as referenced in Polish J. Chemistry 64,741 (1990).

Reaction Scheme C

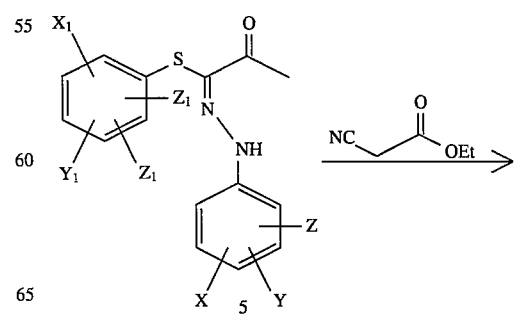

-continued
Reaction Scheme C

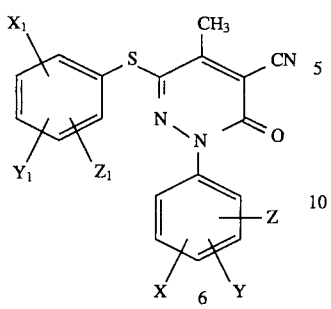

Reaction of compound 5 with ethylcyanoacetate under Knoevenagel conditions with ammonium acetate produces pyridazinone analogs 6. The type of aromatic substitution may require forcing conditions at high temperatures to achieve successfial cyclization.

REACTION SCHEME D

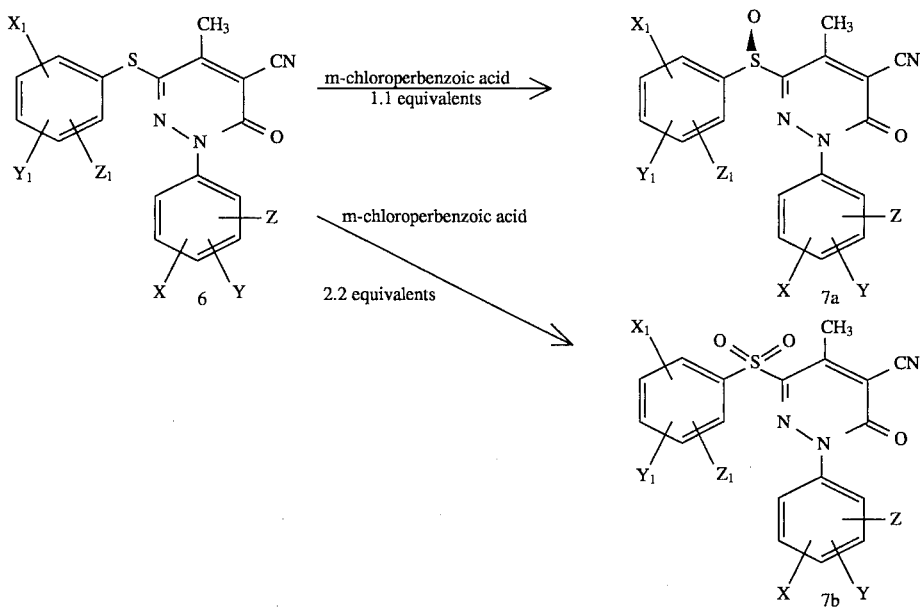

Sulfoxide derivatives 7a are prepared by reaction of compound 6 with 1.1 equivalents of m-chloroperbenzoic acid or with related oxidizing agents. Sulfone derivatives 7 are prepared by reaction of compound 6 with 2.2 equivalents of m-chloroperbenzoic acid or with related oxidizing agents.

The compounds of Formula I in the present invention are also directed to a method for suppressing the immune system in a subject in need of such treatment. These compounds possess immunosuppressive activity, and therefore are useful for the treatment and prevention of the resistance to transplantation or transplantation rejection of organs or tissues (such as heart, kidney, liver, lung, bone marrow, comea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroidiris, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne, Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical comea, dystorphia epithelialis comeae, comeal leukoma, ocular pemphigus, Mooren's ulcer, Scleritis, Graves' ophthalmopathy, severe intraocular inflammation, and the like.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T-cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carders for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carders suitable for use in manufacturing preparations, in solid, semisolid, or liquid form, and in addition auxiliary, stabilizing, thickening and coloring agents and perilLines may be used.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carders, adjuvants and vehicles. The term parenteral as used herein includes subcutaneous injections, intravenous, intramuscular, intrastemal injection or infusion techniques.

For the treatment of reversible obstructive airways disease, it is preferable that the compotmd of Formula I be administered by inhalation to the lung, especially in the form of a powder.

The compounds of Formula I may optionally be employed in co-therapy with anti-proliferative agents. Particularly preferred is co-therapy with an antiproliferative agent selected from the group consisting of: azathioprine, brequinar sodium, deoxyspergualin, mizaribine, mycophenolic acid morpholino ester, cyclosporin, FK-506 and rapamycin.

Dosage levels of the compounds of the present invention are of the order from about 0.005 mg to about 10 mg per kilogram of body weight per day, preferably from about 0.005 mg to about 10 mg per kilogram of body weight per day, are useful in the treatment of the above-indicated conditions (from about 0.35 mg to about 700 mg per patient per day, assuming a 70 kg patient). In addition, the compounds of the present invention may be administered on an intermittent basis; i.e. at daily, semiweekly, weekly, semimonthly or monthly intervals.

The amount of active ingredient that may be combined with the carder materials to produce a single dosage form will vary depending upon the host treated and the particular mode of administration. For example, a formulation intended for the oral administration of humans may contain from 0.5 mg to 1 gm of active agent compounded with an appropriate and convenient amount of carder material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 10% by weight, preferably from 0.001 to 10% by weight, and most preferably from about 0.005 to 2% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

Preparation of 1-Chloro-1-[(4-methoxyphenyl)hydmzono]-2-propanone

A vigorously stirred suspension of 16.75 g(0.136 mole) of 4-methoxyaminobenzene in 960 ml of 1N hydrochloric acid was cooled to 5° C. and treated, dropwise, with 15.8 g of sodium nitrite dissolved in 200 ml of water. The temperature was maintained at 5° C.±1° during the addition. After addition was complete, the reaction mixture was stirred in the cold for an additional 30 min. The pH of the reaction mixture was adjusted to 4.5 with solid sodium acetate (72 g). The resultant mixture was treated, dropwise, with 24 g (0.178 mole) of 3-chloro-2,4-pentanedione dissolved in 200 ml of methanol. After addition was complete, the reaction mixture was allowed to warm to room temperature over the next hour.

The suspension was extracted with 3–300 ml portions of ethyl ether. The combined extracts were washed with 4 volumes of water, dried over magnesium sulfate and filtered. The filtrate was evaporated in vacuo to yield 29 gm of a dark oil. The residue was dissolved in n-hexane:ethyl acetate (2:1) (approximately 400 ml) and the solution was passed over 1000 g of silica gel. Elution with n-hexane:ethyl acetate (3:1) yielded 11.66 g of 1-chloro- 1-[(4-methoxyphenyl)hydrazono]-2-propanone, mp 114°–116° C. (hexane).

$^1$H NMR(400 MHz, CDCl$_3$): 2.53 (s,3H), 3.79 (s,3H) 6.89 (d, J=9 Hz, 2H), 7.24 (d, J=9 Hz, 2H), 8.36 (broad s,1H);

PBBI-NH3/CI-MS Calculated for C$_{10}$H$_{11}$ClN$_2$O$_2$(226.6); found: 227 (M+1), 123

EXAMPLE 2

Preparation of 1-Chloro-1-[(2-chlorophenyl)hydrazono]-2, propanone 2-chloroaminobenzene is reacted with sodium nitrite and 3-chloro-2,4-pentanedione as in Example 1 to yield 1-chloro-1-[(2-chlorophenyl)hydrazono]-2-propanone.

EXAMPLE 3

Preparation of 1-chloro-1-[(3-chlorophenyl)hydrazono]-2-propanone

The reaction of 14.55 (0.113 mole) g of 3-chloroaminobenzene with 13.2 g of sodium nitrite and 20 g of 3-chloro-2,4-pentanedione as in Example 1 yielded 17.45 g of 1-chloro-1-[(4-nitrophenyl)hydrazono]-2-propanone, mp 180°–183° C.

$^1$H NMR(400 MHz, CDCl$_3$): 2.56 (s, 3H), 7.03 (m, 2H), 7.25 (m, 2H), 8.39 (broad s, 1H).

EXAMPLE 4

Preparation of 1-chloro-1-[(4-chlorophenyl)hydrazono]-2-propanone 4-chloroaminobenzene (14.48 g ,0.113 mole) was reacted with 13.2 g of sodium nitrite and 20 g of 3-chloro-2,4-pentanedione as in Example 1. Evaporation of the ether extracts yielded the crude product. Trimration with benzene yielded 10.4 g of 1-chloro-1-[(4-chlorophenyl) hydrazono] -2-propanone, mp 168°–171° C. (C$_6$H$_6$).

$^1$H NMR(400 MHz, CDCl$_3$): 2.54(s,3H), 7.14(d, J=9 Hz,2H), 7.30(d, J=9 Hz, 2H), 8.39(broad s,1H).

EXAMPLE 5

Preparation of 1-chloro-1-[(2-methylphenyl)hydrazono]-2-propanone 2-methylaminobenzene is reacted with sodium nitrite and 3-chloro-2,4-pentanedione as in Example 1 to yield 1-chloro-1-[(2-methyl-phenyl)hydrazono]-2-propanone.

EXAMPLE 6

Preparation of 1-chloro-1-[(3-methylphenyl)hydrazono]-2-propanone

The reaction of 12.14 g of 3-methylaminobenzene with 13.2 g of sodium nitrite and 20 g of 3-chloro-2,4-pentanedione as in Example 1 yielded 18.5 g of 1-chloro-1-[(3-methylphenyl)hydrazono]-2-propanone, mp 144°–146° C.

$^1$H NMR(400 MHz, CDCl$_3$):2.36 (s,3H), 2.55 (s,3H), 6.88 (d, J=7 Hz, 1H), 7.01 (d, J=7 Hz, 1H), 7.23 (m, 2H), 8.39 (broad s,1H)

EXAMPLE 7

Preparation Of 1-chloro-1-[(4-methylphenyl)hydrazonol]-2-propanone

The reaction of 12.1 (0.113 mole) g of 4-methylaminobenzene with 13.2 g of sodium nitrite and 20 g of 3-chloro-2,4-pentanedione as in Example 7 yielded 5.5 g of 1-chloro-1-[(4-methylphenyl)hydrazono]-2-propanone, mp 141°–143° C. (C$_6$H$_6$).

$^1$H NMR(400 MHz, CDCl$_3$):2.51 (s,3H),2.54(s,3H), 7.12 (dd, J=25 Hz, 9 Hz, 4H), 8.39 (broad s, 1H).

EXAMPLE 8

Preparation of 1-chloro-1-[(phenyl)hydrazono]-2-propanone

The reaction of 10.55 g (0.113 mol)of aminobenzene with 13.2 g of sodium nitrite and 20 g of 3-chloro-2,4-pentanedione as in Example 1 yielded 8.95 g of 1-chloro-1-[(phenyl)hydrazono]-2-propanone, mp 132°–134° C.

$^1$H NMR(400 MHz, CDCl$_3$): 2.56 (s, 3H), 7.06 (t, J=7.4 Hz, 1H), 7.23 (t, J=7 Hz, 2H), 7.35 (t, J=7.8 Hz, 2H), 8.42 (broad s, 1H).

EXAMPLE 9

Preparation of 1-chloro-1-[(4-bromophenyl)hydrazono]-2-propanone 4-bromoaminobenzene is reacted with sodium nitrite and 3-chloro-2,4-pentanedione as in Example 1 to yield 1-chloro-1-[(4-bromo-phenyl)hydrazonao-2-propanone.

EXAMPLE 10

Preparation of 1-chloro-1-[(3-nitrophenyl)hydrazono]-2-propanone 3-nitroaminobenzene is reacted with sodium nitrite and 3-chloro-2,4-pentanedione as in Example 1 to yield 1-chloro-1-[(3-nitrophenyl)hydrazono]-2-propanone.

EXAMPLE 11

Preparation of 1-[(4-chlorophenyl)thio]-1-[(4-methoxyphenyl)hydrazonol]-2propanone A suspension of 31.7 g (0.139 mol) of 1-chloro-1-[(4-methoxyphenyl)hydrazono]- 2-propanone in 400 ml of ethanol was treated with 23.4 g (0.161 mole) of 4-chlorothiophenol followed by 23.4 ml of triethylamine. The suspension was heated at reflux for 2 hours and cooled. The resultant suspension was filtered and the precipitate was washed with 1 portion of cold ethanol. The solids were dried in vacuo to yield 35.77 g of 1-[(4-chlorophenyl)thio]-1-[(4-methoxyphenyl)hydrazono]-2-propanone, mp 111.5°–113.5° C.

$^1$H NMR(400 MHz, CDCl$_3$): 2.55 (s,3H), 3.80(s,3H), 6.88 (d, J=8 Hz, 2H), 7.19 (d, J=8 Hz, 2H), 7.13(m, 4H), 9.2 (broad s,1H)

PBBI-NH$_3$,CI-MS Calculated for C$_{16}$H$_{15}$ClN$_2$SO$_2$(334.8); found: 335 (M+1), 234, 124

EXAMPLE 12

Preparation of 1-[(4-chlorophenyl)thio]-1-[(2-chlorophenyl)hydrazono]-2-propanone 1-chloro-1-[(2-chlorophen yl)hydrazono]-2-propanone is reacted with 4-chlorothiophenol as Example 11 to yield 1-[(4-chlorophenyl)thio]-1-[3-chlorophenyl)hydrazono]-2-propanone.

EXAMPLE 13

Preparation of 1-[(4-chlorophenyl)thio]-1-[(4-chlorophenyl) hydrazono]-2-propanone The reaction of 4.47 g of 1-chloro-1-[(4-chlorophenyl) hydrazono]-2-propanone with 3.43 g of 4-chlorothiophenol and 3.36 ml of triethylamine as Example 11 yielded 6.3 g of 1-[(4-chlorophenyl)thio]-1-[(4-chlorophenyl)hydrazono]-2-propanone, mp 164°–167° C.

$^1$H NMR(400 MHz, CDC$_3$) 2.54 (s, 3H), 7.13 (m, 4H), 7.22 (m, 2H), 7.29 (d, J=8.8 Hz, 2H), 9.19 (broad s, 1H),

EXAMPLE 14

Preparation of 1-[(4-chlorophenyl)thio]-1-[(3-chlorophenyl)hydrazono]-2-propanone The reaction of 2.23 g of 1-chloro-1-[(3-chlorophenyl) hydrazono]-2-propanone with 1.72 g of 4-chlorothiophenol as Example 11 yielded 3.14 g of 1-[(4-chlorophenyl)thio]-1-[(3-chlorophenyl)hydrazono]-2-propanone, mp 128°–131° C.

¹H NMR(400 MHz, CDCl₃): 2.56 (s, 3H), 7.03 (dd, J=8.2, 2 Hz, 2H), 7.15 (m, 2H), 7.24 (m, 4H).

EXAMPLE 15

Preparation of 1-[(4-chlorophenyl)thio]-1-[(3-methylphenyl)hydrazono]-2-propanone The reaction of 2.88 g (0.0136 mol) of 1-chloro-1-[(3-methylphenyl)hydrazono]-2-propanone with 2.10 g of 4-chlorothiophenol and 2.04 ml of triethyl amine in 35 ml of ethanol as Example 11 yielded 3.8 g of 1-[(4-chlorophenyl)thio]-1-[(3-methylphenyl)hydrazono]-2-propanone, mp 112°–114° C.

¹H NMR(400 MHz, CDCl₃): 2.35 (s, 3H), 2.57 (s, 3H), 6.89 (d, J=7.6 Hz, 1H), 7.00 (m, 1H), 7.27 (d, J=8.8 Hz, 2H), 7.20 (J=8.4 Hz, 2H), 7.21 (m, 2h), 9.21 (broad s, 1H).

EXAMPLE 16

Preparation of 1-[(4-chlorphenyl)thio]-1-[(phenyl)hydrazono]-2-propanone

The reaction of 951 mg (4.85 mmol) of 1-chloro-1-[(phenyl) hydrazono]-2-propanone with 864 mg of 4-chlorothiophenol and 840 ul of triethylamine in 15 ml of ethanol as Example 11 yielded 347 mg of 1-[(4-chlorophenyl)thio]-1-[(phenyl)hydrazono]-2-propanone, mp 111°–113° C.

¹H NMR(400 MHz, CDCl₃): 2.56 (s, 3H), 7.07 (m, 1H), 7.14 (d, J=8 Hz, 2H), 7.21 (m, 4H), 7.34 (m, 2H), 9.23 (s, 3H).

PBBI-NH3/CI-MS Calculated for $C_{15}H_{13}ClN_2OS$(304); found: 305 (M+1), 204, 160, 94.

EXAMPLE 17

Preparation of 1-[(4-chlorophenyl)thio]-1-[(2-methylphenyl) hydrazono]-2-propanone 1-chloro-1-[(2-methylphenyl)hydrazono]-2-propanone is reacted with 4-chlorothiophenol triethyl amine in ethanol as Example 11 yields 1-[(4-chlorophenyl)thio]-1-[(2omethylphenyl)hydrazono]-2-propanone.

EXAMPLE 18

Preparation of 1-[(4-chlorophenyl)thio]-1-[(4-methylphenyl)hydrazono]-2-propanone The reaction of 4.07(0.0193 mol) g of 1-chloro-1-[(4-methylphenyl-)hydrazono]-2-propanone, 3.43 g of 4-chlorothiophenol and 3.36 ml of triethylamine in 40 ml of ethanol as in Example 11 yielded 5.55 g of 1-[(4-chlorophenyl)thio]-1-[(4-methylphenyl)hydrazono]-2-propanone, mp 133°–135.5° C.

¹H NMR(400 MHz, CDCl₃): 2.38 (s, 3H), 2.55 (s, 3H), 7.14 (m, 8H), 9.21 (broad s, 1H).

EXAMPLE 19

Preparation of 1-[(4-chlorophenyl)thio]-1-[(4-bromophenyl)hydrazono]-2-propanone 1-chloro-1-[(4-bromophenyl)hydrazono]-2-propanone is reacted with 4-chlorothiophenol and triethyl amine in ethanol as Example 11 to yield 1-[(4-chlorophenyl)thio]-1-[(4-bromophenyl)hydrazono]-2-propanone.

EXAMPLE 20

Preparation of 1-[(4-chlorophenyl)thio]-1-[(3-nitrophenyl)hydrazono]-2-propanone 1-chloro-1-[(3-nitrophenyl)hydrazono]-2-propanone is reacted with 4-chlorothiophenol triethyl amine in ethanol as Example 11 to yield 1-[(4-chlorophenyl)thio]-1-[(3-nitrophenyl)hydrazono]-2-propanone.

EXAMPLE 21

Preparation of 1-[(phenyl)thio]-1-[(4-methoxyhenyl)hydrazono]-2-propanone

The reaction of 392 mg of 1-chloro-1-[(4-methoxyphenyl) hydrazono]-2-propanone, 220 mg of thiophenol and 280 ul of triethylamine in 6 ml of ethanol as in Example 11 yielded 440 mg of 1-[(phenyl)thio]-1-[(4-methoxyphenyl)hydrazono]-2-propanone, mp 120°–123° C.

H NMR(400 MHz, CDCl₃): 2.56 (s,3H), 3.77(s,3H), 6.88 (d, J=8 Hz, 2H), 7.13 (d, J=8 Hz, 2H), 7.19 (m, 5H), 9.19 (broad s,1H).

PBBI-NH3/CI-MS Calculated for $C_{16}H_{16}N_2SO_2$(300); found: 301 (M+1), 200, 175, 166

EXAMPLE 22

Preparation of 6-[(4-chlorophenyl)thiol]-2,3-dihydro-2-(4-methoxyphenyl)-5-methyl-3-oxo-4-pyridazinecarbonitile A flasked equiped with a claisen distillation head and magnetic stirring was charged with mixture of 32.6 g (0.097 mole) 1-[(4-chlorophenyl)thio]-1-[(4-methoxyphenyl)hydrazono]-2-propanone, 24.8 ml of ethylcyanoacetate and 12.2 g of ammonium acetate. The mixture was heated under a nitrogen atmosphere at 160° C. for 30 min. The reaction mixture was cooled and dissolved in methylene chloride. The organic layer was washed successively with sat'd aqueous sodium bicarbonate and water. The organic layer was dried over magnesium sulfate and evaporated in vacuo to yield semi pure product. The residue was recrystallized from 1900 ml of ethanol to yield 33.05 g of 6-[(4-chlorophenyl)thio]-2,3-dihydro-2-(4-methoxyphenyl)-5-methyl-3-oxo-4-pyridazinecarbonitrile, mp 146°–148° C. (EtOH).

¹H NMR(400 MHz, CDCl₃) 2.15 (s, 3H),2.53 (s, 3H), 6.84 (d, J=9.2 Hz, 2H), 7.33 (d, J=9.2 Hz, 2H), 7.35 (d, J=8.6 Hz, 2H), 7.40 (d, J=8.6 Hz, 2H).

PBBI-NH3/CI-MS Calculated for $C_{19}H_{14}ClN_3O_2S$ (383.8); Found 383 (M+1)

EXAMPLE 23

Preparation of 6-[(4-chlorpheyl)thio]-2,3-dihydro-2-(3-methylphenyl) 5-methyl-3-oxo-4-pyridazinecarbonitrile The reaction of 930 mg of 1-[(4-chlorophenyl)thio]-1-[3-methylphenyl)hydrazono]-2-propanone, 705 ul of ethylcyano acetate and 380 mg of ammonium acetate as in Example 22, yielded 763 mg of 6-[(4-chlorophenyl)thio]-2,3-dihydro-2-(3-methylphenyl)5-methyl-3-oxo-4-pyridazinecarbonitrile, mp 163°–165° C. (EtOH).

¹H NMR(400 MHz, CDCl₃): 2.29 (s, 3H), 2.54 (s, 3H), 7.11 (m, 2H), 7.23 (m, 3H), 7.28 (d, J=8.8 Hz, 2H), 7.42 (d, J=8.8 Hz, 2H).

PBBI-NH₃/CI-MS Calculated for $C_{19}H_{14}ClN_3OS$ (367.8); Found 368 (M+1)

EXAMPLE 24

Preparation of 6-[(4-chlorophenyl)]-2,3-dihydro-2-(3-chlorophenyl)5-methyl-3-oxo-4-pyridazinecarbonitrile The reaction of 600 mg (1.77 mol) of 1-[(4-chlorophenyl)thio]-1-[4-methoxyphenyl)hydrazono]-2-propanone, 714 ul of ethylcyano acetate and 358 mg of ammonium acetate as in Example 22, yielded 560 mg of 6-[(4-chlorophenyl)thio]-2,3-dihydro-2-(3-chlorophenyl)5-methyl-3-oxo-4-pyridazinecarbonitrile, mp 150°–151° C. (EtOH).

¹H NMR(400 MHz, CDCl₃) 2.55 (s, 3H), 7.25 (m 2H), 7.30 (m, 1H), 7.42 (m, 3H), 7.57 (m, 2H).

PBBI-NH$_3$/CI-MS Calculated for C$_{18}$H$_{11}$Cl$_2$N$_3$OS (388); Found: 390, 388 (M+1), 354, 246, 221.

EXAMPLE 25

Preparation of 6-[(4-chlorophenyl)thio]-2,3-dihydro-2-(4-chlorophenyl) 5-methyl-3-oxo-4-pyridazinecarbonitrile The reaction of 2.0 g (5.9 mmol) of 1-[(4-chlorophenyl)thio]-1-[4-chlorophenyl)hydrazono]-2-propanone, 1.5 ml of ethylcyano acetate and 750 mg of ammonium acetate as in Example 22, yielded1.29 g of 6-(4-chlorophenyl)thio] -2,3-dihydro-2-(4-chlorophenyl)5-methyl-3-oxo-4-pyridazinecarbonitrile, mp 177°–179° C. (EtOH).

$^1$H NMR(400 MHz, CDCl$_3$): 2.54 (S,3H), 7.29 (d, J=9 Hz, 2H), 7.35 (d, J=9 Hz, 2H), 7.37 (d, J=9 Hz, 2H), 7.42 (d, J=9 Hz, 2H)

PBBI-NH$_3$/ CI-MS Calculated for C$_{18}$H$_{11}$Cl$_2$N$_3$OS (404); Found:405 (M+1) 390, 388, 246, 128.

EXAMPLE 26

Preparation of 6-[(4-chlorophenyl)thio]-2,3-dihydro-2-(2-chlorophenyl) 5-methyl-3-oxo-4-pyridazinecarbonitrile 1-[(4-chlorophenyl)thio]-1-[2-chlorophenyl)hydrazono]-2-propanone, ethylcyano acetate and ammonium acetate is reacted as in Example 22, to yield 6-[(4-chlorophenyl)thio] -2,3-dihydro-2-(2-chlorophenyl)5-methyl-3-oxo-4-pyridazinecarbonitrile.

EXAMPLE 27

Preparation of 6-[(4-chlorophenyl)thio]-2,3-dihydro-2-(phenyl)5-methyl-3-oxo-4-pyridazinecarbonitrile The reaction of 1.8 g (5.9 mmol) of 1-[(4-chlorophenyl)thio]-1-[phenyl)hydrmzono]-2-propanone, 1.5 ml of ethylcyano acetate and 750 mg of ammonium acetate as in Example 22, yielded1.29 g of 6-[(4-chlorophenyl)thio]- 2,3-dihydro-2-(4-chlorophenyl)5-methyl-3-oxo-4-pyridazinecarbonitrile, mp 180°–182° C. (EtOH).

$^1$H NMR(400 MHz, CDCl$_3$):

PBBI-NH$_3$/ CI-MS Calculated for C$_{18}$H$_{11}$Cl$_2$N$_3$OS (404); Found:405 (M+1) 390, 388,246, 128.

EXAMPLE 28

Preparation of 6-[(4-chlorophenyl)thiol-2,3-dihydro-2-(2-methylphenyl)5-methyl-3-oxo-4-pyridazinecarbonitrile 1-[(4-chlorophenyl)thio]-1-[2-methylphenyl)hydrazono]-2-propanone, ethylcyano acetate and ammonium acetate is reacted as in Example 22, to yield 6-[(4-chlorophenyl)thio] -2,3-dihydro-2-(2-methylpheynyl)5-methyl-3-oxo-4-pyridazinecarbonitrile.

EXAMPLE 29

Preparation of 6-[(4-chlorophenyl)thio]-2,3-dihydro-2-(4-bromophenyl) 5-methyl-3-oxo-4-pyridazinecarbonitrile 1-[(4-chlorophenyl)thio]-1-[4-bromophenyl)hydrazono]-2-propanone, ethylcyano acetate and ammonium acetate is reacted as in Example 22, to yield 6-[(4-chlorophenyl)thio] -2,3-dihydro-2-(4-bromophenyl)5-methyl-3-oxo-4-pyridazinecarbonitrile.

EXAMPLE 30

Preparation of 6-[(4-chlorophenyl)thio]-2,3-dihydro-2-(3-nitrophenyl) 5-methyl-3-oxo-4-pyridazinecarbonitrile 1-[(4-chlorophenyl)thio]-1-[3-nitrOphenyl)hydrazono]-2-propanone, ethylcyano acetate and ammonium acetate is reacted as in EXAMPLE 22, to yield 6-[(4-chlorophenyl)thio]-2,3-dihydro-2-(3-nitrophenyl)5- methyl-3-oxo-4-pyridazinecarbonitrile.

EXAMPLE 31

Preparation of 6-[(4-chlorophenyl)thio]-2,3-dihydro-2-(4-methylphenyl) 5-methyl-3-oxo-4-pyridazinecarbonitrile The reaction of 1.86 g (5.83 mmol)of 1-[(4-chlorophenyl)thio]-1-[4-methylphenyl)hydrazono]-2-propanone, 1.5 ml of ethylcyano acetate and 750 mg of ammonium acetate as in Example 22, yielded 914 mg of 6-[(4-chlorophenyl)thio]-2,3-dihydro-2-(4-methylphenyl)5-methyl-3-oxo-4-pyridazinecarbonitrile, mp 190°–192° C. (EtOH).

$^1$H NMR(400 MHz, CDCl$_3$): 2.33 (s, 3H), 2.53 (s, 3H), 7.13 (d, J=8.8 Hz, 2H), 7.27 (d, J=8.8 Hz, 2H), 7.35 (d, J=8.8 Hz, 2H), 7.41 (d, J=8.8 Hz, 2H).

PBBI-NH$_3$/ CI-MS Calculated for C$_{19}$H$_{14}$ClN$_3$OS(367.8); Found: 368 (M+1), 226, 147, 108.

EXAMPLE 32

Preparation of 6-[(phenyl)thio]-2,3-dihydro-2-(4-methoxyphenyl)-5-methyl-3-oxo-4-pyridazinecarbonitrile The reaction of 429 mg of 1-[(phenyl)thio]-1-[(4-methoxyphenyl)hydrazono]-2-propanone, 375 ul of ethylcyanoacetate and 178 mg of ammonium acetate as in Example 55, yielded 165 mg of 6-[(phenyl)thio]- 2,3-dihydro-2-(4-methoxyphenyl)-5-methyl-3-oxo-4-pyridazinecarbonitrile, mp 179°–180° C. (EtOH).

$^1$H NMR(400 MHz, CDCl$_3$): 2.53 (s. 3H), 3.78 (s, 3H), 6.98 (d, J=9.2 Hz, 2H), 7.36 (d, J=9.2 Hz, 2H), 7.37 (m, 3H), 7.42( m, 2H).

PBBI-NH$_3$/ CI-MS Calculated for C$_{19}$H$_{15}$N$_3$O$_2$S (349.4); Found: 350 (m+1), 244, 217.

EXAMPLE 33

Preparation of 6-[(phenyl)sulfony]-2,3-dihydro-2-(4-methoxyphenyl)-5-methyl-3-oxo-4-pyridazinecarbonitrile A solution of of 6-[(phenyl)thio]-2,3-dihydro-2-(4- methoxyphenyl)-5-methyl-3-oxo-4-pyridazine is treated with 1.1 equivalent of 80% 3-chloroperoxybenzoic acid. The reaction mixture is stirred at room temperature for 16 hours. The solvent is removed in vacuo and the product is isolated by preparative thin layer chromatography. Elution with methylene chloride:2-propanol (100:2) yields 6-[(phenyl)sulfonyl]-2,3-dihydro-2-(4-methoxyphenyl)-5-methyl-3-oxo-4-pyridazinecarbonitrile.

EXAMPLE 34

Preparation of 1-chloro-1-[(4-methoxyphenyl)hydrazono]-2-propanone

A preferred method for the preparation of the titled compound is as follows:

A vigorously stirred suspension of 49.2 g (0.339 mole) of 4-methoxyaminobenzene in 400 ml of 5N hydrochloric acid was cooled to 0° C. and treated, dropwise, with 30.4 g (0.440 mol) of sodium nitrite dissolved in 100 ml of water. The temperature was maintained at 0°–5° C.±1° during the addition. After addition was complete, the reaction mixture was stirred at 0° C.±1° for an additional 30 min. The cold diazonium solution was poured slowly into a vigorously stirred solution of 54 g (0.401 mol) of 3-chloro-2,4-pentanedione dissolved in 280 ml of pyridine and 280 ml of water precooled to –8° C.±1°. The ice bath was removed and the resultant yellow suspension was stirred at 5° C.±1° for 30 minutes and diluted with 500 ml of water. The yellow solids were collected by filtration and washed with 300 ml water (4 times). The wet crude product was dissolved in 500 ml of methylene chloride. The organic layer was dried over magnesium surfate, filtered and evaporated in vacuo to yield 56.45 g of 1-chloro-1-[(4-methoxyphenyl)hydrazono]-2-propanone. The purity of the product was sufficient for further utilization. Further purification was accomplished by chromatography over silica gel and elution with elution with n-hexane:ethyl acetate (3:1) to yield 1-chloro-1-[(4-methoxyphenyl)hydrazono]-2-propanone, mp 114°–116° C. (hexane).

$^1$H NMR(400 MHz, CDCl$_3$): 2.53 (s,3H), 3.79 (s,3H) 6.89 (d, J=9 Hz, 2H), 7.24 (d, J=9 Hz, 2H), 8.36 (broad s, 1H);

PBBI-NH$_3$/ CI-MS Calculated for C$_{10}$H$_{11}$ClN$_2$O$_2$(226.6); found: 227 (M+1), 123

EXAMPLE 35

T Cell Proliferation Assay

Spleens form C57B 1/6 mice were taken under sterile conditions and gently dissociated in ice-cold RPMI 1640 culture medium (GIB C, Grand Island, N.Y.) supplemented with 10% heat inactivated fetal calf serum (GIBO). Cells were pelleted by centrifugation at 1500 rpm for 8 minutes. Contaminating red cells were removed by treating the pellet with ammonium chloride lysing buffer (GIBO) for 2 minutes at 4° C. Cold medium was added and cells were again centrifuged at 1500 rpm for 8 minutes. T lymphocytes were then isolated by separation of the cell suspension on nylon wool columns as follows:

Nylon wool columns were prepared by packing approximately 4 gms of washed and dried nylon wool into 20 ml plastic syringes. The colunms were sterilized by autoclaving at 25° F. for 30 minutes. Nylon colunms were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from columns with warm culture medium and the cell suspensions were spun as described above.

Purified T lymphocytes were resuspended at 2.5×10$^5$ cells/ml in complete culture medium composed of RPMI 1640 medium with 10% heat-inactivated fetal calf serum, 100 mM glutamine, 1 mM sodium pyruvate, 2×10$^{-5}$M 2-mercaptoethanol and 50 ug/ml gentamycin. Ionomycin was added at 250 ng/ml and PMA at 10 ng/ml. The cell suspension was immediately distributed into 96 well flat-bottom microculture plates (Costar) at 200 ul/well. The various dilutions of test compound were then added in triplicate wells at 20 ul/well. The culture plates were then incubated at 37° C. in a humidified atmosphere of 5% CO$_2$–95% air for 44 hours. The proliferation of T lymphocytes was assessed by measurement of tritiated thymidine incorporation. After 44 hours of culturing, the cells were pulselabelled with 2 uCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results were expressed as concentration of compound required to inhibit tritated thymidine uptake of T cells by 50%.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

EXAMPLE 36

T Cell IL-2 Assay

Peripheral blood mononuclear cells from healthy donors were separated by density centrifugation with ficoll-hypaque (LSM, Organon Teknika, Durham, N.C.), followed by rosetting with neuraminidase treated SRBC. After another centrifugation with LSM, the SRBC of the rosetted T cells were then lysed with ammonium chloride lysing buffer (GIBCO). Such purified T cells were resuspended at 3×10$^6$/ml in RPMI 1640 culture medium (GIBCO, Grand Island, N.Y.) supplemented with 10% fetal calf serum (HyClone Laboratories, Logan, Utah), 100 mM glutamine, 1 mM sodium pymvate, 0.1 mM non-essential amino acids, and 1% penn-strep (GIBCO). The cell suspension was immediately distributed into 96 well round-bottom microculture plates (Costar) at 200 ul/well. The various dilutions of test compound were then added in triplicate wells at 25 ul/well, incubated for 15 min at 37° C. Ionomycin (125 ng/ml), anti-CD28 (100 ng/ml) and PMA (1 or 5 ng/ml, with ionomycin or anti-CD28, respectively) were added to the appropriate wells. The culture plates were then incubated at 37° C. in a humidified atmosphere of 5% CO$_2$–95% air for 24 hours. The supernatants were removed, and assayed for IL-2 with an IL-2 ELISA Kit (Collaborative Biomedical Products, Bedford. MA). Mean OD and units of IL-2 of the replicate wells were calculated and the results were expressed as concentration of compound required to inhibit IL-2 production of T cells by 50%.

What is claimed is:

1. A compound of formula I

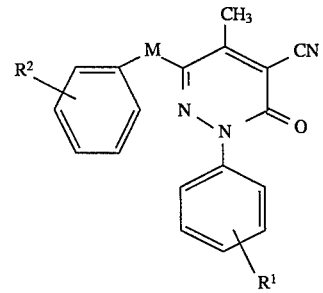

or a pharmaceutically acceptable salt, hydrate or crystal form thereof, wherein:

when M is S, R$^1$ and R$^2$ are selected from the following combinations:
when R$^2$ is 4-chloro, then R$^1$ is 4-OCH$_3$, 2-CH$_3$, 4-Cl, 4-CH3, 3-Cl,
3-CH3, 2-Cl, 4-H, 4-Br, 3-NO$_2$; and
when R$^2$ is H, then R$^1$ is 4-OCH$_3$, and
when M is —SO$_2$—, then R$^2$ is J and R$^1$ is 4-OCH$_3$.

2. The compound of claim 1, selected from the group consisting of:
6-[(4-chlorophenyl)thio]-2,3-dihydro-2-(4-methoxyphenyl)-5-methyl-3-oxo-4-pyridazinecarbonitrile;

6-[(4-chlorophenyl)thio]-2,3-dihydro-2-(3-methylphenyl)5-methyl-3-oxo-4-pyridazinecarbonitrile; 6-[(4-chlorophenyl)thio]-2,3-dihydro-2-(3-chlorophenyl)5-methyl-3-oxo-4-pyridazinecarbonitrile; 6-[(4-chlorophenyl)thio]-2,3-dihydro-2-(4-chlorophenyl)5-methyl-3-oxo-4-pyridazinecarbonitrile; 6-[(4-chlorophenyl)thio]-2,3-dihydro-2-(2-chlorophenyl)5-methyl-3-oxo-4-pyridazinecarbonitrile; 6-[(4-chloropheyl)thio]-(2,3-dihydro-2-(phenyl)5-methyl-3-oxo-4-pyridazinecarbonitrile;
6-[(4-chlorophenyl)thio]-2,3-dihydro-2-(2-methylphenyl)5-methyl-3-oxo-4-pyridazinecarbon; 6-[(4-chlorophenyl)thio]-2,3-dihydro-2-(4-bromophenyl)5-methyl-3-oxo-4-pyridazinecarbonitrile; 6-[(4-chlorophenyl)thio]-2,3-dihydro-2-(3-nitrophenyl)5-methyl-3-oxo-4-pyridazinecarbonitrile;
6-[(4-chlorophenyl)thio]-2,3-dihydro-2-(4-methylphenyl)5-methyl-3-oxo-4-pyridazinecarbonitrile-6-[(phenyl)thio]-2,3-dihydro-2-(4-methoxyphenyl)5-methyl-3-oxo-4-pyridazinecarbonitrile;
6-[(phenyl)sulfonyl]-2,3-dihydro-2-(4-methoxyphenyl)-5-methyl-3-oxo-4-pyridazinecarbon 1-chloro-1-[(4-methoxyphenyl)hydrazono]-2-propanone.

3. A pharmaceutical formulation comprising a pharmaceutically acceptable carrier and a therapeutically effective amount of the compound of claim 1 or a pharmaceutically acceptable salt, crystal form or hydrate thereof.

4. The pharmaceutical formulation of claim 3, comprising in addition, an antiproliferative agent selected from the group consisting of: azathioprine, brequinar sodium, deoxyspergualin, mizaribine, mycophenolic acid morpholino ester, cyclosporin, FK-506 and rapamycin.

5. A method of suppressing the immune system in a subject in need thereof, which comprises the administration to the subject of an immune suppressing amount of the compound of claim 1.

6. The method of claim 5, comprising the concomitant administration of an antiproliferative agent.

7. The method of claim 6, wherein the antiproliferative agent is selected from the group consisting of azathioprine, brequinar sodium, deoxyspergualin, mizaribine, mycophenolic acid morpholino ester, cyclosporin FK-506 and rapamycin.

* * * * *